(12) United States Patent
Manougian

(10) Patent No.: US 6,986,773 B1
(45) Date of Patent: Jan. 17, 2006

(54) HUMAN AIRWAY CLEARING TOOL

(76) Inventor: Edward Manougian, 1517 Summit Rd., Berkeley, CA (US) 94708-2216

( * ) Notice: Subject to any disclaimer, the term of this patent is extended or adjusted under 35 U.S.C. 154(b) by 383 days.

(21) Appl. No.: 10/325,092

(22) Filed: Dec. 20, 2002

Related U.S. Application Data

(63) Continuation-in-part of application No. 09/685,747, filed on Oct. 11, 2000, now abandoned.

(51) Int. Cl.
   *A61D 1/12* (2006.01)

(52) U.S. Cl. .................................... 606/106

(58) Field of Classification Search ............... 606/106, 606/160, 161, 162
   See application file for complete search history.

(56) References Cited

U.S. PATENT DOCUMENTS 3,581,745 A * 6/1971 Eller ........................ 606/106
5,709,691 A * 1/1998 Morejon .................... 606/106

* cited by examiner

*Primary Examiner*—Kevin T. Truong
(74) *Attorney, Agent, or Firm*—John D. Gugliotta

(57) ABSTRACT

A human airway cleaning tool is provided that aids in the removal of foreign or blocking material in the airway of humans. Resembling a Yankauer suction tube, the cleaning tube has a provision for the attachment of a conventional vacuum cleaner hose. This feature makes the invention suitable for use anywhere at almost anytime as long as a vacuum cleaner is available. Further featured is a round, ball-shaped, tip that easily enters a person's throat with causing damage. Shaped such that it is easily held, the cleaning tool is easily maneuvered while it is in a person's mouth.

4 Claims, 3 Drawing Sheets

HUMAN AIRWAY CLEARING TOOL

RELATED APPLICATIONS

The present invention was first described in Disclosure Document No. 476,328, filed on Jul. 3, 2000 in accordance with MPEP § 1706, and is a continuation-in-part of U.S. Utility patent application Ser. No. 09/685,747 filed on Oct. 11, 2000, now abandoned.

BACKGROUND OF THE INVENTION

1. Field of the Invention

The present invention relates generally to instruments for removing foreign objects from the throat or connected passageways and, more particularly, to a portable human airway clearing tool for use with an otherwise conventional hose type vacuum cleaner.

2. Description of the Related Art

In the related art, doctors and other emergency medical personnel have the capability to quickly remove food or other blocking matter from a person's airway using Yankauer suction tubes or other similar devices. While the effectiveness of these devices are characterized by the countless lives saved, these devices have the problem of only being able to be used where a medical grade vacuum source is available. Many people, in homes, restaurants and the like have died waiting for the availability of such devices and a suitable vacuum source.

Particular limitations of Yankauer suction tubes create further needs within the field. For example, the Yankauer suction tube is not for removing solids. Solids can only be removed with forceps once the airway is exposed. This is because of the lack of an adequate suction seal due to a plurality of suction orifices rather than a single suction orifice. As a result, such a device is only adequate for removing fluids.

A search of the prior art did not disclose any patents that read directly on the claims of the instant invention; however, the following references were considered related in that they provide for hand-held application of vacuum for various purposes.

The following patents disclose a hand-held fetal vacuum extractor.

U.S. Pat. No. 6,074,399 issued in the name of Wallace et al.;
U.S. Pat. No. 5,281,229 issued in the name of Neward;
U.S. Pat. No. 5,224,947 issued in the name of Cooper et al.; and
U.S. Pat. No. 5,163,944 issued in the name of Neward.

The following patents describe a suction device for withdrawing an object obstructed the breathing passage of a choking victim.

U.S. Pat. No. 5,741,269 issued in the name of McCredy; and
U.S. Pat. No. 5,609,149 issued in the name of Takach;
U.S. Pat. No. 6,030,318, issued in the name of Howard, discloses a method and system of selectively exercising parts of a human body with a vacuum;
And, U.S. Pat. No. 4,883,047, issued in the name of Guitay, describes a vacuum apparatus for massaging the human body.

Consequently, there exists a need for a means by which choking victims can be assisted by vacuum removal of the offending material without reliance on medical teams and associated medical equipment.

SUMMARY OF THE INVENTION

Therefore, it is an object of the invention to provide for a portable instrument for removing foreign objects from the throat or connected passageways.

It is another object of the present invention to provide a portable human airway clearing tool for use with an otherwise conventional hose type vacuum cleaner.

Briefly described according to one embodiment of the present invention, a human airway clearing tool is a medical apparatus that aids in the removal of foreign material blocking the airway of humans. The present invention has a provision for the attachment of a conventional vacuum cleaner hose. This feature makes the invention suitable for use anywhere at almost anytime as long as a vacuum cleaner is available. This quick response time provides the extra seconds that are necessary to save a person's life and prevent permanent damage. The invention utilizes a round, ball-shaped tip that easily enters a person's throat without causing damage. The invention is shaped such that it is easily held and maneuvered while it is in a person's mouth.

The use of the present invention provides a means to quickly remove foreign matter from a person's airway in a safe manner almost anywhere a vacuum cleaner is present, thus saving lives.

Additionally, the present invention works with a conventional vacuum cleaner, allowing utilization of the invention almost anywhere without the need to wait for hospitals or emergency personnel and equipment.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the FIGS. 1–5.

1. Detailed Description of the Figures

Figure 1:
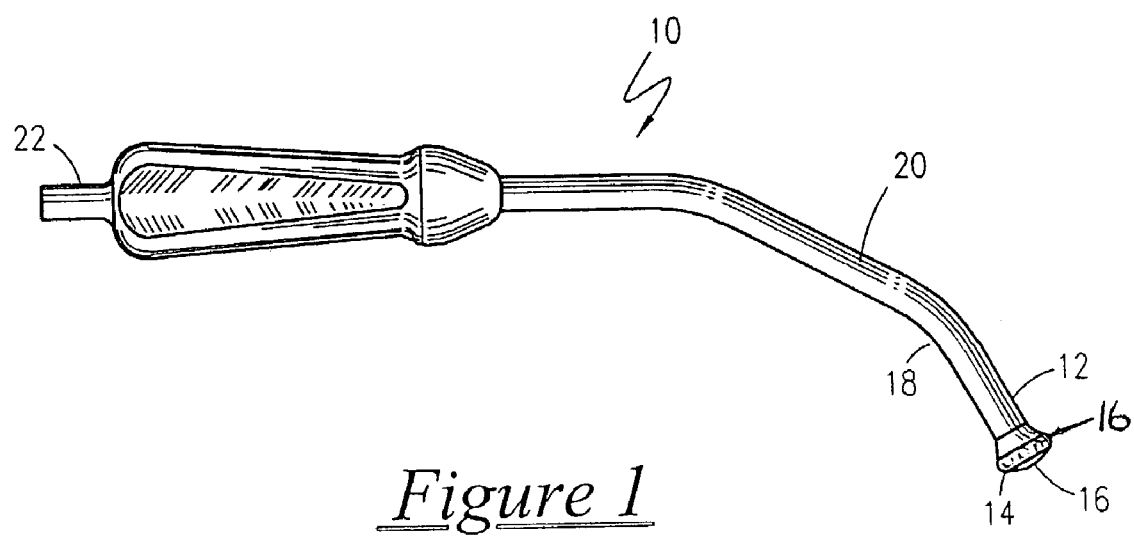
FIG. 1 is a side elevational view of a Yankauer suction tube according to the PRIOR ART.

Referring now to FIG. 1, Yankauer suction tube 10 is shown according to the generally available Prior Art. The Yankauer 10 has at one end a hollow tip 12. The hollow tip has at it's terminal end a ball shaped head 14 for receiving body fluids. It contains several openings 16 through which the body fluids to be aspirated enter. The ball shaped head 14 is fitted onto neck 18 which may be cylindrical in configuration or it may be eliminated so that the ball shaped head 14 directly connects to the delivery port 20. Neck 18 terminates and has as it's other end delivery port 20.

Delivery port 20 is in fluid communication with the ball shaped head 14 and a suction attachment 22 for attaching to a vacuum source.

Figure 2:
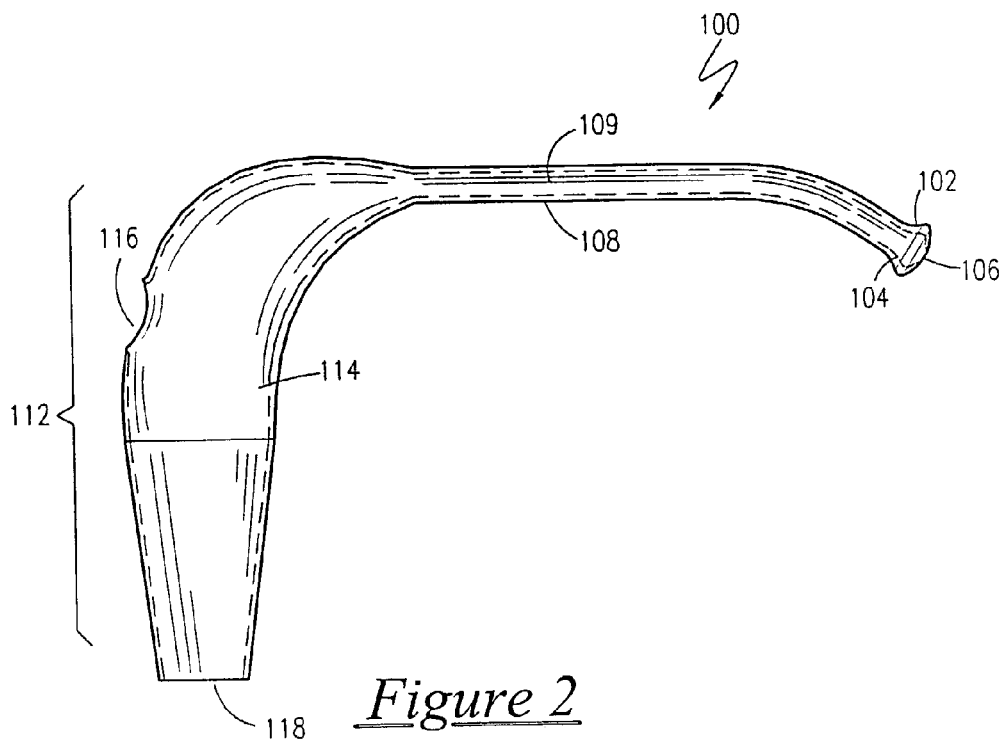
FIG. 2 is a side elevational view of a human airway clearing tool according to preferred embodiment of the present invention.
Figure 3:
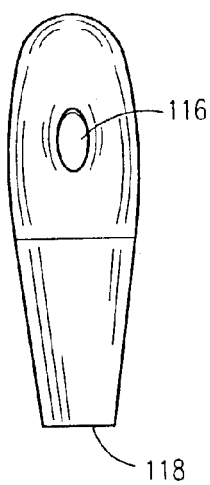
FIG. 3 is a front elevational view thereof.
Figure 4:
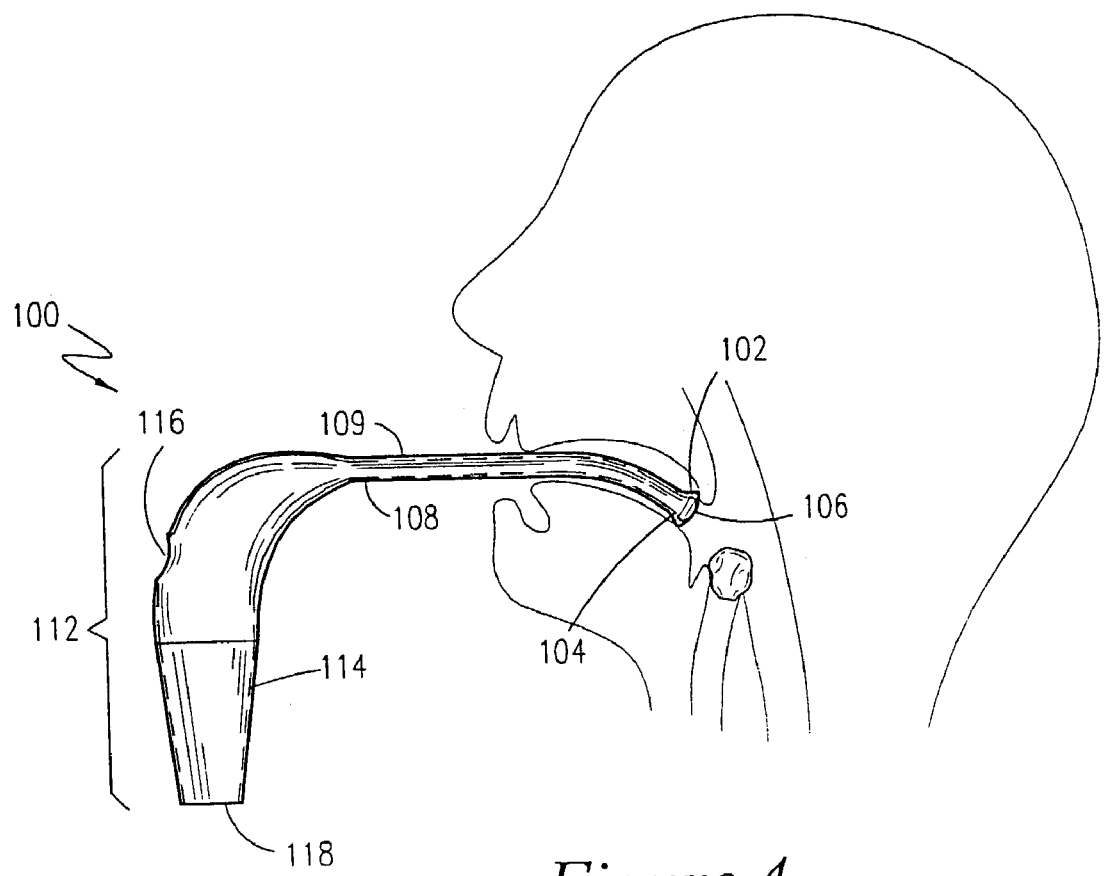
FIG. 4 is a cross sectional side elevational view thereof shown in use to dislodge foreign objects from the throat or connected passageways.
Figure 5:
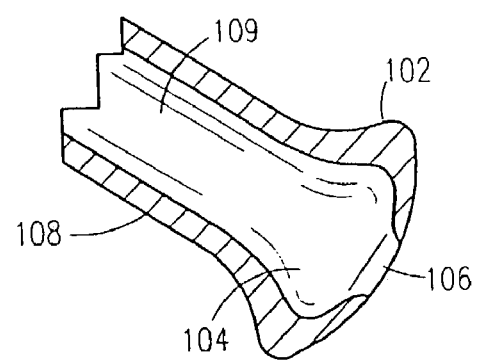
FIG. 5 is an exploded cross sectional view of a suction tip for use with the present invention.

By comparison, FIG. 2, FIG. 4 and FIG. 5 are side elevational views of a human airway clearing tool 100 according to preferred embodiment of the present invention. The clearing tool 100 is anticipated and designed for use with an otherwise conventional hose type vacuum cleaner (not shown) to aid in the removal of foreign or blocking material in the airway of humans. The clearing tool 100 has at one end a hollow tip 102. As best shown in conjunction with FIG. 5, the hollow tip 102 has at it's terminal end a ball shaped head 104 that contains an opening 106 through which the airway obstruction to be aspirated enters. The ball shaped head 104 is shaped in order to form a seal within the victim's throat sidewalls behind the tongue and below the uvula. This "seal" allows for increased directional alignment of suction to the opening 106 by preventing blow-by or leakage of air around the tip 104. The tip 102 is angularly positioned to the end of an elongated neck 108 directed appropriately slightly downward from the horizontal centerline of the neck 108 to allow for the proper positioning of the head 104. The neck 108 is linearly elongated and cylindrical in configuration, and forms an internal conduit 109 in fluid communication with the opening 106. A downwardly curved arm 112 terminates and connects to the neck 108. As best shown in conjunction with FIG. 3, the arm 112 forms a handle 114 which contains and forms a suction control orifice 116 which communicates with the internal conduit 109, and located in the curved arm 112. If the handle 112 is held with the suction control orifice 116 is closed then its terminal end 118 will form the only exit path in fluid communication with the opening 106. The handle 112 is held with the suction control orifice 116 open then its terminal end 118 will form the one of two exit paths in fluid communication with the opening 106. By covering or releasing the suction control orifice 116, airflow can be controlled through the internal conduit 109 from the tip 102. The tip 102, neck 108, the internal conduit 109 and the curved arm 112 are all integrally formed in a one-piece rigid body. This provides sufficient control when in use for directing and manipulating the tip within the airway. It is intended that this one-piece, rigid body is capable of being made of injection molded plastic, preferably clear or translucent so the user can see the obstruction being removed as it is suctioned into the internal conduit.

In a hospital setting, the effectiveness of the Yankauer relies on its tip being immersed in the fluid (blood, mucus, saliva, etc.) That is to be aspirated. This is because the vacuum system utilized by hospitals provides for a high pressure vacuum seal, but does not provide a very effective unsealed vacuum. The immersion of the Yankauer in the fluid prevents air leakage in a hospital vacuum system. The present invention need not be in contact with the obstruction which is to be removed, since the vacuum system it uses provides greater lift, is more tolerant of leakage, and therefore can suck the solid obstruction to it, as is the function of the household vacuum cleaner or other similar devices.

The terminal end 118 of the handle 112 is formed in a tapered, cylindrical fashion. Such a taper will allow for frictional fitting of a tubular vacuum cleaner hose of any commercially available size to the end in order to provide a vacuum source for suction air flow.

2. Operation of the Preferred Embodiment

In operation, the present invention is in conjunction with a hose type vacuum cleaner. If an individual is choking, the Heimlich maneuver should be tried first. If that fails or it is not possible to perform, then the vacuum cleaner is turned on and the tapered handle 118 is placed into its hose. The victim's head is tilted back, and the mouth opened by placing the user's index finger near the back of the tongue with the user's thumb under the chin. By squeezing the thumb and index finger together, the jaw is pulled forward, allowing positioning of the hollow tip 102 within the throat, pressed gently between the back of the tongue and back of the throat. Upon positioning the opening 106 adjacent to any obstruction and increasing suction by covering the suction control orifice 116, the obstruction can be pulled from the throat.

As designed, a device embodying the teachings of the present invention is easily applied. The foregoing description is included to illustrate the operation of the preferred embodiment and is not meant to limit the scope of the invention. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. As one can envision, an individual skilled in the relevant art, in conjunction with the present teachings, would be capable of incorporating many minor modifications that are anticipated within this disclosure. Therefore, the scope of the invention is to be broadly limited only by the following claims.

What is claimed is:

1. A human airway clearing tool to aid in the removal of foreign or blocking material in the airway of humans, said clearing tool comprising:
   a hollow tip having at its terminal end a ball shaped head that contains an opening;
   an elongated neck having said hollow tip angularly positioned at one end directed slightly downward from the horizontal centerline of said neck;
   an internal conduit formed within said neck in fluid communication with said opening such as to allow for use with an otherwise conventional hose type vacuum cleaner;
   a downwardly curved arm terminating and connecting to said neck opposite said hollow tip; and
   wherein said tip, said neck, said internal conduit, and said downwardly curved arm are formed in a rigid body.

2. The clearing tool of claim 1, wherein said neck is linearly elongated and cylindrical in configuration.

3. The clearing tool of claim 1, wherein said arm forms a handle which contains and forms a suction control orifice which communicates with said internal conduit.

4. The clearing tool of claim 3, wherein a terminal end of said handle is formed in a tapered, cylindrical fashion such as will allow for frictional fitting of a tubular vacuum cleaner hose in order to provide a vacuum source for suction air flow.

* * * * *